US00PP23307P2

(12) United States Plant Patent
Blom

(10) Patent No.: US PP23,307 P2
(45) Date of Patent: Jan. 1, 2013

(54) ***FESTUCA* PLANT NAMED 'CASCA11'**

(50) Latin Name: *Festuca glauca*
Varietal Denomination: Casca11

(76) Inventor: Annemarie Blom, Haarsteeg (NL)

( * ) Notice: Subject to any disclaimer, the term of this patent is extended or adjusted under 35 U.S.C. 154(b) by 0 days.

(21) Appl. No.: 13/199,515

(22) Filed: Sep. 1, 2011

(51) Int. Cl.
*A01H 5/00* (2006.01)

(52) U.S. Cl. ..... Plt./384
(58) Field of Classification Search ..... Plt./384
See application file for complete search history.

*Primary Examiner* — Annette Para
(74) *Attorney, Agent, or Firm* — Penny J. Aguirre

(57) ABSTRACT

A new cultivar of *Festuca glauca*, 'Casca11', characterized its cascading foliage that is intensely silver-blue in color with the coloration retained throughout the growing season, and its tolerance to heat and humidity and drought.

2 Drawing Sheets

Botanical classification: *Festuca glauca.*
Varietal denomination: 'Casca11'.

BACKGROUND OF THE INVENTION

The present invention relates to a new and distinct cultivar of *Festuca glauca* and will be referred to hereafter by its cultivar name, 'Casca11'. 'Casca11' is a new cultivar of perennial ornamental grass grown for container and landscape use.

The new cultivar, 'Casca11' arose as a naturally occurring chimeral mutation of *Festuca glauca* 'Elijah Blue' (not patented) that was growing in the Inventor's garden in 2002 in Haarsteeg, The Netherlands.

Asexual reproduction of the new cultivar was first accomplished by division in Haarsteeg, The Netherlands in 2004 by the Inventor. The characteristics of this cultivar have been determined to be stable and are reproduced true to type in successive generations.

SUMMARY OF THE INVENTION

The following traits have been repeatedly observed and represent the characteristics of the new cultivar. The new *Festuca* has not been observed under all possible environmental conditions. These attributes in combination distinguish 'Casca11' from all other selections of *Festuca* known to the Inventor.

1. 'Casca11' exhibits foliage that is intensely silver-blue in color with the coloration retained throughout the growing season.
2. 'Casca11' exhibits cascading foliage.
3. 'Casca11' is tolerant to heat and humidity and drought.

'Casca11' has a similar plant habit and growth rate to its parent plant, 'Elijah Blue', however 'Casca11' exhibits leaves that are more silver-blue in color. In addition to 'Elijah Blue', 'Casca11' can be most closely compared to the cultivars 'Bolder Blue' (not patented) and 'Select' (not patented). Both 'Bolder Blue' and 'Select' differ from 'Casca11' in having leaves that are more upright and less cascading and in being smaller in plant size.

BRIEF DESCRIPTION OF THE DRAWING

The accompanying colored photographs illustrate the overall appearance and distinct characteristics of two year-old plants as grown in 16-cm containers outdoors in Rijnsburg, The Netherlands.

The photograph in FIG. 1 illustrates the overall plant habit and appearance of 'Casca11'.

Figure 1:
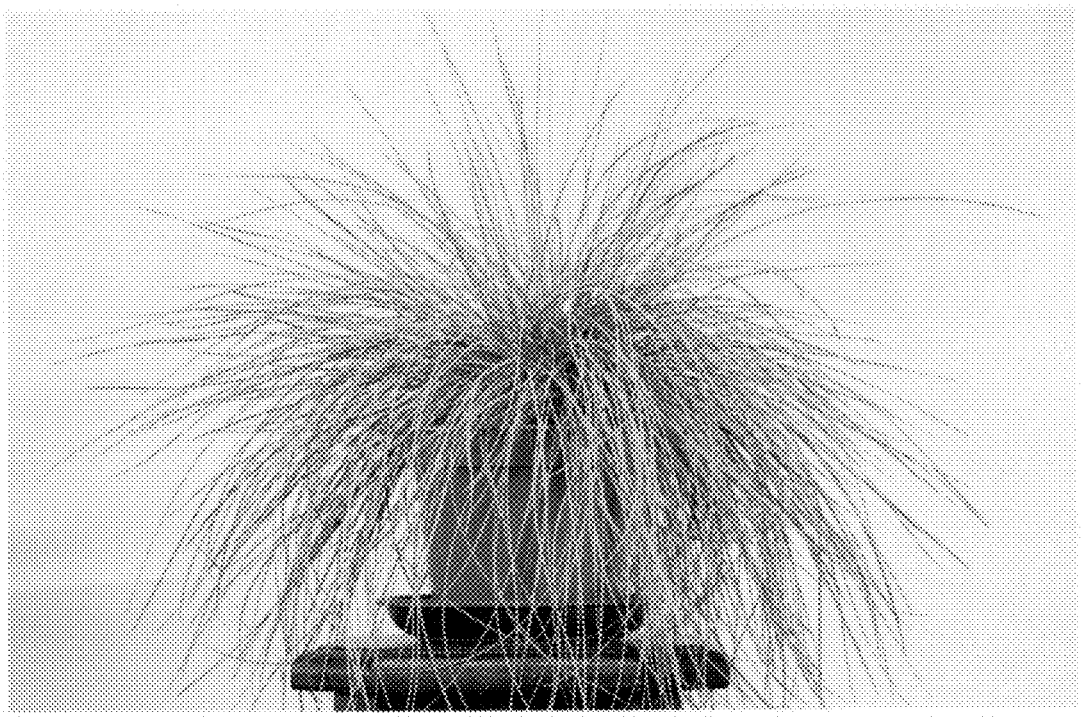
Figure 2:
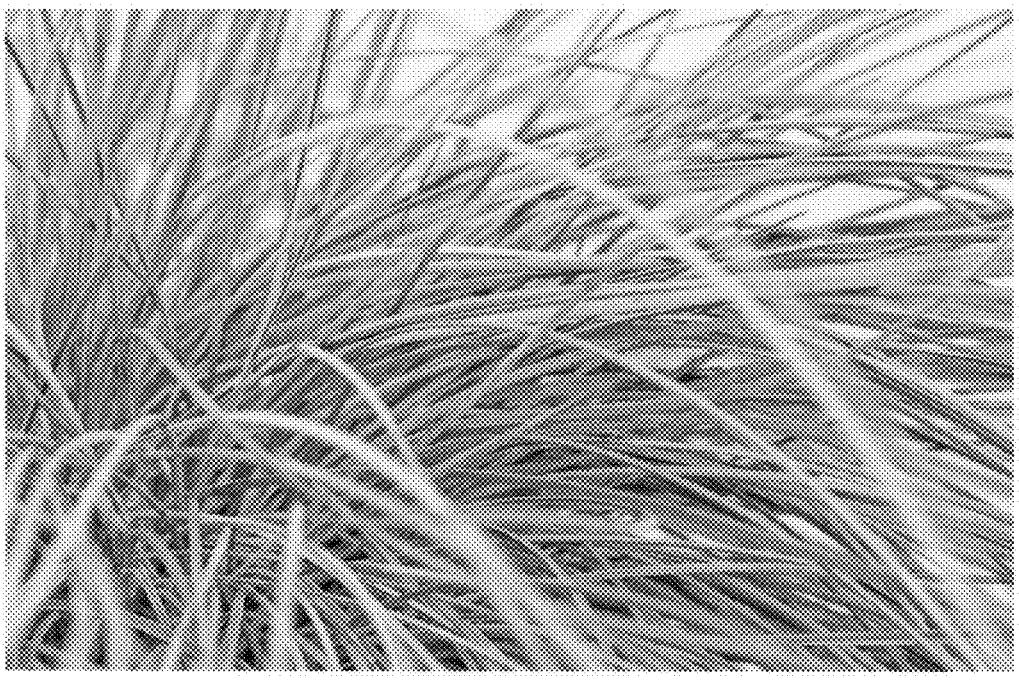

The photograph in FIG. 2 provides a detailed close-up view of the leaf coloration of 'Casca11'.

Figure 3:
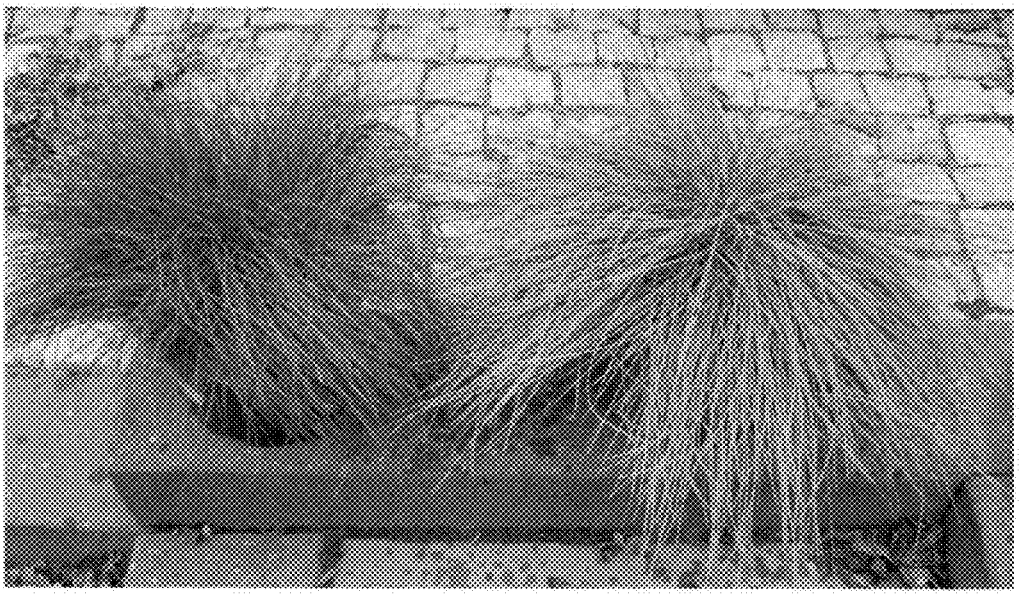

The photograph in FIG. 3 shows a comparison between 'Elijah Blue' on the left and 'Casca11' on the right.

The colors in the photograph may differ slightly from the color values cited in the detailed botanical description, which accurately describe the colors of the new *Festuca.*

DETAILED BOTANICAL DESCRIPTION

The general observations and descriptions describe 2-year old plants as grown outdoors in 16-cm containers in Rijnsburg, The Netherlands. Plants were grown under average day temperature of 12° to 28° C. and average night temperatures of 6° to 16° C. The phenotype may vary somewhat with variations in temperature, day-length, light intensity, soil types, and water and fertility levels without, however, any variance in genotype. The color determinations are in accordance with the 2007 R.H.S. Colour Chart of The Royal Horticultural Society, London, England, except where general color terms of ordinary dictionary significance are used.

General description:

*Plant type.*—Evergreen to semi-evergreen perennial grass.

*Plant habit.*—Tight mound of cascading foliage.

*Height and spread.*—Reaches about 33.2 cm in height, spreads to about 68.5 cm in diameter.

*Hardiness.*—U.S.D.A. Zones 4 to 8.

*Culture.*—Tolerant to heat, humidity and drought.

*Diseases and pests.*—No susceptible or resistance to pests and diseases has been observed.

*Root description.*—Fibrous.

Growth and propagation:

*Propagation.*—Division.

*Root development from division.*—Fully develop in 9-cm containers in about 9 months.

*Growth rate.*—Moderate to high.

*Branching.*—Main shoots grow from the base, no lateral branches.

Foliage description:

*Leaf shape.*—Filiform, strongly curved.

*Leaf division.*—Simple.

*Leaf base.*—Sheathed.

*Leaf apex.*—Long acuminate.

*Leaf aspect.*—Leaves initially emerge upright, then cascade.

*Leaf venation.*—Parallel, color same as leaf blade.

*Leaf margins.*—Entire.

*Leaf persistence.*—Persistent; evergreen under conditions tested.

*Leaf size.*—Average of 28.9 cm in length and 1.8 mm in width.

*Leaf number.*—Average of 4 leaves per shoot, about 200 shoots in a 16-cm container.

*Leaf arrangement.*—Tufted.

*Leaf surface.*—Dull and smooth on upper and lower surface.

*Leaf durability to stress.*—High.

*Leaf color.*—Young leaves upper surface; N138C, lighter towards the base; 144B to 144C, leaves covered with a waxy layer; 189B, mature leaves upper surface; N137C to 137D, leaves covered with a waxy layer; 188A, sheaths; 138D, young leaves lower surface; N138C, lighter towards the base; 144B to 144C, leaves covered with a waxy layer; 189B, mature leaves lower surface; N137C to N137D, leaves covered with a waxy layer; 188A, sheaths; 138D.

Flower description: No flowers observed to date.

Fruits and seeds: Seed production has not been observed to date.

It is claimed:

1. A new and distinct cultivar of *Festuca* plant named 'Casca11' as herein illustrated and described.

* * * * *